United States Patent [19]

Paumard

[11] Patent Number: 5,827,939
[45] Date of Patent: Oct. 27, 1998

[54] HETEROPOLYACID CATALYSTS IN THE PREPARATION OF ESTERS OF UNSATURATED CARBOXYLIC ACIDS

[75] Inventor: Eric Paumard, Cappel, France

[73] Assignee: Atochem, Paris, France

[21] Appl. No.: 171,880

[22] Filed: Dec. 22, 1993

Related U.S. Application Data

[63] Continuation of Ser. No. 713,254, Jun. 13, 1991, abandoned.

[30] Foreign Application Priority Data

Jun. 13, 1990 [FR] France .................................. 90 07368

[51] Int. Cl.⁶ .............................. C07C 67/04; B01J 21/02
[52] U.S. Cl. .......................... 560/205; 560/217; 560/247; 252/432; 252/437; 252/439; 252/469; 252/470; 252/467
[58] Field of Search ..................................... 560/205, 217, 560/244; 252/432, 437, 439, 469, 470, 467

[56] References Cited

U.S. PATENT DOCUMENTS

| | | |
|---|---|---|
| 3,442,934 | 5/1969 | Pine . |
| 3,442,935 | 5/1969 | Pine . |
| 4,205,182 | 5/1980 | Izumi et al. ............................. 560/247 |

FOREIGN PATENT DOCUMENTS 458236  12/1936  United Kingdom .

OTHER PUBLICATIONS

Kulikov et al, "Acidic properties of Heteropolyacids and the mechanism of their catalytic action in homogeneus acid–type reactions", Mekh. Katal. Reakts., 3$^{rd}$ vol. 2, 13–16. 1982 ((Russian Language) abstract–only included here.).

Chemical Abstracts, vol. 9, No. 6, issued 1982 (Columbus, Ohio, USA), S. M. Kulikov et al., "Acidic Properties of heteropolyacids . . . ", the abstract No. 44047u, Mekh. Katal. Reakts., Mater. Uses, Konf., 3$^{rd}$, vol. 2, 13–16. (Russ.).

Kulikov et al, "Acidic Properties of heteropolyacids and the mechanism for their catalytic Acition in homogeneous–acid–type RKNS", Mekh. Katal. Reakts., Mater. Uses. Konp., 3$^{rd}$, vol. 2, 13–16., 1982.

Primary Examiner—Keith D. MacMillan
Attorney, Agent, or Firm—Millen, White, Zelano & Branigan, P.C.

[57] ABSTRACT

Use of at least one heteropolyacid $H_n A_a D_c O_y \cdot xH_2O$ where A is phosphorus, boron, silicon, germanium, tin, arsenic, antimony, copper, nickel, cobalt, iron, cerium, thorium, chromium and mixtures thereof; D is molybdenum, tungsten, vanadium and combinations thereof; a is 0.1–10; c is 6–18; n is the number of acidic hydrogens in the heteropolyacid and is a number above 1; y is the number of oxygens in the heteropolyacid and is a number of 10–70; and x is the number of moles of water of crystal-lisation and is a number of 0–40, as catalyst in the preparation of esters of unsaturated carboxylic acids by direct esterification of acids with alcohols or by transesterification, these reactions being carried out in the liquid phase.

34 Claims, No Drawings

HETEROPOLYACID CATALYSTS IN THE PREPARATION OF ESTERS OF UNSATURATED CARBOXYLIC ACIDS

This application is a continuation of application Ser. No. 07/713,254, filed Jun. 13, 1991 ABN.

BACKGROUND OF THE INVENTION

The present invention relates to the use of heteropolyacids as catalysts in the liquid-phase preparation of esters of unsaturated carboxylic acids, especially acrylic acid and methacrylic acid, by direct esterification of these acids with alcohols, or by transesterification, and to the corresponding preparation process.

In the reactions of the type indicated above, which are advantageously conducted under mild conditions of temperature (for example less than 100° C.) and pressure (atmospheric pressure or reduced pressure)—which avoids polymerization of the ester in the course of its preparation—an acid catalyst of the Bronsted or Lewis type, such as sulphuric acid or alkyl titanate, is generally used. However, such an acid presents pollution and corrosion problems, and it is rapidly deactivated.

Furthermore, in Japanese Patent Application No. 175 5731/1980, a process for the preparation of a (meth)acrylate is described which comprises the reaction of (meth)acrylic acid with a lower alcohol at elevated temperature in the gaseous phase in the presence of molecular oxygen and a catalyst having the structure of a heteropolyacid containing phosphorus and molybdenum.

In addition, heteropolyacids are known as catalysts in the reaction of olefins with acids, for example of ethylene with acrylic acid, such as is described in French Patent No. 2,404,621, the reaction being carried out at elevated temperatures and pressures.

SUMMARY OF THE INVENTION

It has now been found that the use of heteropolyacids in the liquid-phase preparation of esters of unsaturated carboxylic acids by esterification or transesterification makes it possible to inhibit the formation of byproducts, thus leading to the desired esters with high conversion rates and high selectivities, while avoiding all of the disadvantages of sulfuric acid. For this reason especially the reaction times are shorter and the pollution and corrosion problems are eliminated. Moreover, heteropolyacids are catalysts in homogeneous medium which can be recycled in batchwise processes.

Accordingly, the present invention first relates to the use of at least one heteropolyacid of the general formula:

$$H_n A_a D_c O_y \cdot xH_2O$$

in which:
A represents phosphorus, boron, silicon, germanium, tin, arsenic, antimony, copper, nickel, cobalt, iron, cerium, thorium, chromium or a mixture of at least two of these elements;
D represents molybdenum, tungsten, vanadium or a combination of at least two of these elements;
a is a number from 0.1 to 10;
c is a number from 6 to 18;
n is the number of acidic hydrogens in the heteropolyacid and is a number above 1;
y is the number of oxygens in the heteropolyacid and is a number in the order of 10 to 70; and
x is the number of moles of water of crystallisation and is a number from 0 to about 40, as catalyst in the preparation of esters of unsaturated carboxylic acids by direct esterification of said acids with alcohols or by transesterification, these reactions being carried out in the liquid phase.

The present invention also relates to a process for the preparation of an ester of an unsaturated carboxylic acid by a direct liquid-phase esterification reaction of said acid with an alcohol or by a transesterification reaction in the presence of an acid catalyst, characterized in that the catalyst used is at least one heteropolyacid of the general formula shown above.

These heteropolyacids are known and can be prepared by known techniques. Particularly advantageous heteropolyacids are phosphomolybdic acid ($H_3PMo_{12}O_{40}$), phosphotungstic acid ($H_3PW_{12}O_{40}$) and silicotungstic acid ($H_4SiW_{12}O_{40}$).

The catalysts used in the reaction are used in a suitable manner as components of a liquid mixture in dissolved form. According to the present invention, the homogeneous liquid mixture gives advantageous results because the efficiency of contact is markedly higher.

The concentration of the catalyst according to the invention in the reaction mixture in the liquid phase can vary widely. For homogeneous catalysts of this type, it is more appropriate to establish the catalyst concentration as a function of the concentration of the minor reactant in mole per mole of acid or in mole per mole of alcohol. Thus, it has been found to be preferable to use molar concentrations of about $1 \cdot 10^{-3}$ to $5 \cdot 10^{31\ 2}$.

The operating conditions for the liquid-phase esterification and transesterification reactions can vary widely; however, in standard practice, the temperature can be between about 20° and 200° C., and the reaction is usually carried out at atmospheric pressure or under a pressure below atmospheric pressure. In the context of the process of the present invention, the reactions carried out at temperatures of 60° to 130° C., while using a pressure below atmospheric pressure, for example below $6 \times 10^4$ Pa, turn out to be particularly advantageous. The duration of the reaction can likewise vary within wide limits; it can be short, for example a few minutes, or several hours depending on the state of the catalyst used, the reaction temperature and the pressure. The molar ratio of alcohol to acid or to ester can vary as long as the predominant product is the desired ester. Suitably, the molar ratios are about 0.1 to about 3 mole of alcohol per mol of starting acid or ester.

The alcohol used for the esterification or transesterification reaction is, for example, a saturated primary, secondary or tertiary monoalcohol having 1 to 22 carbon atoms, such as propanol, methanol, ethanol, n-butanol, isopropanol, sec-butanol, tert.-butanol, 2-ethylhexanol; an ether alcohol of the formula $C_nH_{2n+1}$—O—$C_nH_{2n+1}$—OH in which n is an integer ranging from 1 to 5, such as methoxyethanol, ethoxyethanol, methoxymethanol and ethoxymethanol; a polyol, such as ethylene glycol, propylene glycol, 1,3-butanediol, 1,4-butanediol, 1,6-hexanediol, neopentyl glycol, 1,4-cyclohexanediol, 1,4-cyclohexanedimethanol, 2,2,4-trimethyl-1,3-pentanediol, 2-ethyl-2-methyl-1,3-propanediol, 2,2-diethyl-1,3-propanediol, diethylene glycol, dipropylene glycol, triethylene glycol, tripropylene glycol, tetraethylene glycol, tetrapropylene glycol, trimethylolethane, trimethylolpropane, glycerol, pentaerythritol and mono- or polyethoxylated and mono- or polypropoxylated polyols.

The use of polymerization inhibitors is in general desirable in order to avoid polymerisation of the unsaturated esters and/or acids present. Phenols, such as hydroquinone, hydroquinone methyl ether, di-tert.-butylcatechol or p-anilinophenol, aromatic amines in the presence of oxygen, N,N-diethylhydroxylamine, nitrobenzene, phenothiazine, di(2-ethylhexyl)octylphenyl phosphite, methylene blue and mixtures thereof in all proportions are preferably used for this purpose. The polymerization inhibitors are in general used in amounts of 0.05–1% by weight, relative to the total weight of the reactants involved in the reaction.

Furthermore, the reaction according to the invention can be carried out in the presence of an inert solvent capable of performing the function of azeotropic agent of the water formed in the reaction. The heteroazeotrope formed between the water and said solvent settles. The aqueous phase is collected and the solvent present in the organic phase is returned to the reaction. The solvent can be chosen especially from:

saturated alcohols having 1 to 4 carbon atoms, light aromatic hydrocarbons, such as benzene, aliphatic ketones, such as methyl isobutyl ketone, linear and cyclic alkanes having 6 or 7 carbon atoms, such as hexane, cyclohexane, heptane and methylcyclohexane.

The solvent is in general used in an amount of up to about 50% by weight in the reaction medium (reactants +solvent).

The reactions according to the invention are advantageously carried out in a reactor suitable for a liquid-phase reaction. For this reason it is possible to use a container which is stirred or not stirred and heated and contains the reactants with the catalyst dissolved therein. In a batchwise operation, the products are separated by fractional distillation using distillation columns. Since the anion of the heteropolyacid has the tendency to decompose upon contact with heavy metal ions, such as iron and nickel, it is desirable that the material of which the reactor is made does not release such metal ions. For example, an enamelled steel reactor may be used.

In addition, in accordance with the invention, at the end of the esterification or transesterification reaction the crude reaction product can be subjected to distillation and the residue containing the catalyst and, if present, the polymerization inhibitor(s), which is(are) reused in a new esterification or transesterification operation, can be recovered, it being possible for such a recycling of the catalyst to take place several times.

The examples below illustrate the present invention without, however, limiting its scope. From the analytical results of the reaction product of each example, the composition of the product and then the catalyst performance are determined by the three criteria of conversion, selectivity and yield, which are defined as follows:

(a) in the case of direct esterification

% conversion (C)=(moles of acid reacted/moles of acid fed)×100

% selectivity (S)=(moles of ester obtained/moles of acid reacted×100

% yield (Y)=(moles of ester obtained/moles of acid fed)×100

(b) in the case of transesterification

% conversion (C)=(moles of alcohol reacted/moles of alcohol fed)×100

% selectivity (S)=(moles of ester obtained/moles of alcohol reacted)×100

% yield (Y)=(moles of ester obtained/moles of alcohol fed)×100

EXAMPLE 1

Transesterification between ethyl acrylate and butanol 550 g (5.5 mol) of ethyl acrylate, 220 g (3 mol) of butanol and 21 g of catalyst $H_3PW_{12}O_{40}$ ($7.25 \times 10^{-3}$ mol), i.e. $2.4 \times 10^{-3}$ mol per mole of butanol, are placed in a 1-liter glass autoclave equipped with a mechanical stirrer and fitted with a reflux column, a condenser and a receiver. 1.5 g of hydroquinone (0.2% by weight relative to the reactant feed) are introduced. While stirring, the pressure is lowered to $6 \times 10^4$ Pa, and the temperature is brought to 95° C. by means of a heating jacket. The reaction of the alcohol with the light ester is then carried out; in the course of the reaction, the ethanol liberated is removed in the form of an azeotrope using ethyl acrylate. After a reaction of 5 hours, the mixture is cooled to ambient temperature, and the product is analysed by gas-phase chromatography. The results are shown in Table 1.

EXAMPLE 2

Transesterification between methyl methacrylate and butanol 550 g (5.5 mol) of methyl methacrylate are reacted with butanol in the same apparatus as that used in Example 1 and under the same conditions as in this example, except that the reaction is carried out for 7 hours.

The results are listed in Table 1.

TABLE 1

| Example | C | S | Y |
| --- | --- | --- | --- |
| 1 | 98 | 73 | 71.5 |
| 2 | 82 | 95 | 78 |

EXAMPLE 3

Direct esterification of acrylic acid with butanol 216 g (3 mol) of acrylic acid, 290 g (3.9 mol) of butanol and 21 g of catalyst $H_3PW_{12}O_{40}$ ($7.2 \times 10^{-3}$ mol), i.e. $2.4 \times 10^{-3}$ mol per mole of acrylic acid, are placed in the same apparatus as that used in Example 1. 0.1% by weight of hydroquinone and 0.1% by weight of phenothiazine relative to the reactant feed is introduced. The procedure is as in Example 1, except that a reaction temperature of 90° C. and a pressure of $1.5 \times 10^4$ Pa are used. The reaction is carried out for 3 hours.

The results are listed in Table 2.

EXAMPLES 4 and 5

After distillation of the unconverted reactants of the crude product from Example 3 and of butyl acrylate, a new identical charge of alcohol and acid is placed on the distillation residue containing the catalyst and the polymerization inhibitors, and the reaction is carried out under the same conditions (Example 4).

This same operation is restarted once again (Example 5), starting with the distillation residue from Example 4.

The results are listed in Table 2.

EXAMPLES 6 and 7

Examples 3 and 4 are both repeated under the same conditions, except that the catalyst is replaced by $H_3PMo_{12}O_{40}$ and that the reaction is carried out for 2.5 hours in Example 6 and for 2 hours in Example 7. The results are likewise listed in Table 2.

TABLE 2

| Example | Nature of catalyst | C | Y | S |
|---|---|---|---|---|
| 3 | $H_3PW_{12}O_{40}$ | 99 | 92.4 | 93.3 |
| 4 | Recycling of the residue from Example 3 | 98 | 85.6 | 87.3 |
| 5 | Recycling of the residue from Example 4 | 97 | 80.5 | 83 |
| 6 | $H_3PMo_{12}O_{40}$ | 99 | 90 | 91 |
| 7 | Recycling of the residue from Example 6 | 97 | 84.4 | 87 |

EXAMPLES 8 to 11

Direct esterification of acrylic acid with butanol using different catalysts

The reaction is carried out in a 1-liter reactor, without mechanical stirring, provided with a reflux column, a condenser and a receiver, so that as the reaction progresses, the most volatile product, i.e. the water of reaction, is separated by distillation as it is formed.

The experimental procedure is the same as in Example 3, with a charge of 3 mol of acrylic acid and 3.9 mol of butanol, to which $2.5 \times 10^{-3}$ mol of catalyst is added per mole of acid, and 0.1% by weight of hydroquinone and 0.1% by weight of phenothiazine, relative to the reactant feed, are added as polymerisation inhibitors, the reaction time being shown in Table 3.

TABLE 3

| Example | Nature of catalyst | Reaction time (min) | Y | C | S |
|---|---|---|---|---|---|
| 8 | $H_3PW_{12}O_{40}$ | 255 | 93.6 | 98 | 95.6 |
| 9 | $H_3PMo_{12}O_{40}$ | 315 | 89.7 | 92.8 | 96.7 |
| 10 | $H_4SiW_{12}O_{40}$ | 200 | 93.3 | 96.3 | 97 |
| 11 (comparative) | $H_2SO_4$ | 670 | 86.9 | 98.1 | 89 |

The results show a substantially higher reactivity of the catalysts of the invention compared with sulphuric acid.

EXAMPLES 12 to 21

Direct esterification of (meth)-acrylic acid with different alcohols using $H_4SiW_{12}O_{40}$ as catalyst The procedure is that of Examples 8 to 11, with a charge of 3 mol of acid, except for Examples 15 and 16 (2 mol), and an alcohol/acid molar ratio such as is indicated in Table 4, and the optional presence of an azeotropic solvent in an amount of 30% by weight of the charge, in order to entrain the water. The catalyst is used in an amount of $2.5 \times 10^{-3}$ mol per mole of acid. The temperatures, pressures and reaction times and the results are shown in Table 4 (for Examples 17, 18 and 21, the selectivity given is that of the sum of mono-, di- and triacrylates formed).

TABLE 4

| Example | Alcohol | Acid | Reaction time (min) | Alcohol/acid molar ratio | Azeotropic solvent | T °C. | P ($10^4$ Pa) | Y | C | S |
|---|---|---|---|---|---|---|---|---|---|---|
| 12 | butanol | MAA | 570 | 1.3 | butanol | 80 | 1.3 | 94.4 | 96.2 | 98.8 |
| 13 | 2-ethylhexanol | AA | 350 | 1.1 | MIBK | 90 | 1 | 93.5 | 96 | 97.3 |
| 14 | " | MAA | 320 | 1.1 | MIBK | 95 | 1 | 84 | 86.8 | 97 |
| 15 | lauryl alcohol | AA | 240 | 1.1 | heptane | 81 | 2.5 | 90.5 | 98.4 | 92 |
| 16 | " | MAA | 330 | 1.1 | " | 95 | 2.5 | 91.5 | 99.3 | 92.1 |
| 17 | ethylene glycol | AA | 350 | 0.47 | " | 85 | 3 | 50 | 87.4 | 57(a) |
| 18 | " | MAA | 450 | 0.47 | " | 80 | 2.5 | 20 | 59 | 34(b) |
| 19 | methoxyethanol | AA | 270 | 1.1 | benzene | 80 | 4.2 | 89 | 92 | 97 |
| 20 | " | MAA | 420 | 1.1 | " | 83 | 4.2 | 83.7 | 78.1 | 99 |
| 21 | tripropylene glycol | AA | 1000 | 0.46 | heptane | 80 | 4.7 | 25 | 55 | 46(c) |

MAA: methacrylic acid
AA: acrylic acid
MIBK: methyl isobutyl ketone
(a) of which 39% diacrylate and 18% monoacrylate
(b) of which 26% diacrylate and 8% monoacrylate
(c) of which 25.5% tripropylene glycol diacrylate, 10.5% tripropylene glycol monoacrylate and 10% dipropylene glycol diacrylate The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosure of all applications, patents, and publications, cited above and below, and of corresponding French Application 90 07368, filed Jun. 13, 1990, are hereby incorporated by reference.

(In this application, where a range of numbers "from x to y" is set forth, both x and y are intended to be included.)

What is claimed is:

1. A process for the preparation of an alpha-ethylenically unsaturated carboxylic acid ester by a direct liquid-phase esterification reaction of said acid with an alcohol in the presence of an acid catalyst, wherein said catalyst is at least one heteropolyacid of the general formula $$H_n A_a D_c O_y \cdot xH_2O$$

in which:

A is phosphorus, boron, silicon, germanium, tin, arsenic, antimony, copper, nickel, cobalt, iron, cerium, thorium, chromium, or a mixture of at least two of these elements;

D is molybdenum, tungsten, vanadium, or a combination of at least two of these elements;

a is a number from 0.1 to 10;

c is a number from 6 to 18;

n is the number of acidic hydrogen atoms in the heteropolyacid and is a number above 1;

y is the number of oxygen atoms in the heteropolyacid and is a number from 10 to 70; and x is the number of moles of water of crystallization and is a number from 0 to 40.

2. A process according to claim 1, wherein the heteropolyacid is phosphomolybdic acid, phosphotungstic acid, silicotungstic acid, or mixtures thereof.

3. A. A process according to claim 1, wherein the catalyst is used in an amount of $1 \times 10^{-3}$ to $5 \times 10^{-2}$ mol per mole of minor reactant.

4. A process according to claim 1, wherein the reaction is carried out at a temperature of between 20° C. and 200° C. at atmospheric pressure or at a pressure below atmospheric pressure.

5. A process according to claim 1, wherein a molar ratio of alcohol to starting acid or ester of 0.1:1 to 3:1 is used.

6. A process according to claim 1, wherein the reaction is carried out in the presence of at least one polymerization inhibitor in an amount of 0.05–1% by weight, relative to the total weight of the reactants.

7. A process according to claim 1, wherein the reaction is carried out in the presence of an inert solvent.

8. A process according to claim 1, wherein at the end of the reaction, the crude reaction product is subjected to distillation, and the residue containing the catalyst and any polymerization inhibitor is reused in a new direct esterification operation.

9. A process according to claim 7, wherein the inert solvent is (a) at least one saturated alcohol having 1 to 4 carbon atoms, (b) at least one light aromatic hydrocarbon, (c) at least one aliphatic ketone, or (d) at least one linear or cyclic alkane having 6 or 7 carbon atoms.

10. A process according to claim 7, wherein the solvent is used in an amount of up to 50% by weight in the reaction medium.

11. A process according to claim 9, wherein the solvent is used in an amount of up to 50% by weight in the reaction medium.

12. A process according to claim 1, wherein the reaction is direct esterification of acrylic acid with butanol to obtain butye acrylate.

13. A process according to claimed 10, wherein the reaction is direct esterification of acrylic or methacrylic acid with butanol, 2-ethyl hexanol, lauryl alcohol, ethylene glycol, methoxyethanol, or tripropylene glycol to obtain the corresponding acrylate or methacrylate.

14. A process according to claim 12, wherein the heteropolyacid is phosphomolybdic acid, phosphotungstic acid, silicotungstic acid, or mixtures thereof.

15. A process according to claim 12, wherein the molar yield of ester, based on the moles of acid fed, is at least 90%.

16. A process according to claim 15, wherein the reaction to obtain the lower yield of at least 90% is conducted in the absence of oxygen.

17. A process according to claim 1, wherein the reaction is carried out at a temperature of 30° C. to 600° C., and at a pressure of less than atmospheric pressure.

18. A process according to claim 1, wherein the reaction is carried out at a temperature of less than 100° C., and at a pressure of less than atmospheric pressure.

19. A process according to claim 1, wherein the reaction is carried out at a temperature of 30° C. to 1000° C., and at a pressure of less than atmospheric pressure.

20. A process according to claim 1, wherein the reaction is carried out at a temperature of 60° C. to 130° C., and at a pressure of less than atmospheric pressure.

21. A process according to claim 1, wherein the alcohol is a saturated monoalcohol having 1 to 22 carbon atoms, an ether alcohol of the formula $C_nH_{2n+1}$—O—$C_nH_{2n+1}$—OH wherein n is an integer of 1 to 5, a polyol, a mono- or polyethoxylated polyol, or a mono- or polypropoxylated polyol.

22. A process according to claim 21, wherein the alcohol is n-propanol, methanol, ethanol, n-butanol, isopropanol, sec-butanol, tert-butanol, 2-ethylhexanol, methoxyethanol, ethoxyethanol, methoxymethanol, ethoxymethanol, ethylene glycol, propylene glycol, 1,3butanediol, 1,4-butanediol, 1,6-hexanediol, neopentyl glycol, 1,4-cyclohexanediol, 1,4-cyclohexanedimethanol, 2,2,4-trimethyl-1,3-pentanediol, 2-ethyl-2-methyl-1,3-propanediol, 2,-diethyl-1,3-propanediol, diethylene glycol dipropylene glycol, triethylene glycol, tripropylene glycol, tetraethylene glycol, tetrapropylene glycol, trimethylolethane, trimethylolpropane, glycerol or pentaerytlitol.

23. A process for the preparation of an alphaethylenically unsaturated carboxylic acid ester by a liquidphase transesterification reaction of said acid with an alcohol in the presence of an acid catalyst, wherein said transesterification is conducted at a temperature of 60° to less than 100° C. and said catalyst is at least one heteropolyacid of the general formula

in which:

A is phosphorus, boron, silicon, germanium, tin, arsenic, antimony, copper, nickel, cobalt, iron, cerium, thorium, chromium, or a mixture of at least two of these element;

D is molybdenum, tungsten, vanadium, or a combination of at least two of these elements;

a is a number from 0.1 to 10;

c is a number from 6 to 18;

n is the number of acidic hydrogen atoms in the heteropolyacid and is a number above 1;

y is the number of oxygen atoms in the heteropolyacid and is a number from 10 to 70; and x is the number of moles of water of crystallization and is a number from 0 to 40.

24. A process according to claim 23, wherein the starting acid used in the direct esterification is acrylic acid or methacrylic acid, and the alcohol used is a saturated monoalcohol having 1 to 22 carbon atoms, an ether alcohol of the formula $C_nH_{2n+1}OC_nH_{2n+1}OH$, in which n is an integer ranging from 1 to 5, a polyol, a mono- or polyethoxylated polyol, or a mono- or polypropoxylated polyol.

25. A process according to claim 23, wherein the reaction is transesterification between ethyl acrylate and butanol to obtain butyl acrylate.

26. A process according to claim 23, wherein the reaction is transesterification between methyl methacrylate and butanol.

27. A process according to claim 25, wherein the heteropolyacid is phosphomolybdic acid, phosphotungstic acid, silicotungstic acid, or mixtures thereof.

28. A process according to claim 26, wherein the heteropolyacid is phosphomolybdic acid, phosphotungstic acid, silicotungstic acid, or mixtures thereof.

29. A process according to claim 23, wherein D is molybdenum, vanadium, or a combination thereof.

30. A process according to claim 23, wherein the alcohol is a saturated monoalcohol having 1 to 22 carbon atoms, an ether alcohol of the formula $C_nH_{2n+1}-O-C_nH_{2n+1}-OH$ wherein n is an integer of 1 to 5, a polyol, a mono- or polyethoxylated polyol, or a mono- or polypropoxylated polyol.

31. A process according to claim 30, wherein the alcohol is n-propanol, methanol, ethanol, n-butanol, isopropanol, sec-butanol, tert-butanol, 2-ethylhexanol, methoxyethanol, ethoxyethanol, methoxymethanol, ethoxymethanol, ethylene glycol, propylene glycol, 1,3-butanediol, 1,4-butanediol, 1,6-hexanediol, neopentyl glycol, 1,4-cyclohexanediol, 1,4-cyclohexanedimethanol, 2,2,4-trimethyl-1,3-pentanediol, 2-ethyl-2-methyl-1,3-propanediol, 2,-diethyl-1,3-propanediol, diethylene glycol dipropylene glycol, triethylene glycol, tripropylene glycol, tetraethylene glycol, tetrapropylene glycol, trimethylolethane, trimethylolpropane, glycerol or pentaerythritol.

32. A process for the preparation of an alpha-ethylenically unsaturated carboxylic acid ester consisting of a direct liquid-phase esterification reaction of said acid with an alcohol in the presence of an acid catalyst, wherein said catalyst is at least one heteropolyacid of the general formula $$H_nA_aD_cO_y \cdot xH_2O$$

in which:

A is phosphorus, boron, silicon, germanium, tin, arsenic, antimony, copper, nickel, cobalt, iron, cerium, thorium, chromium, or a mixture of at least two of these elements;

D is molybdenum, tungsten, vanadium, or a combination of at least two of these elements;

a is a number from 0.1 to 10;

c is a number from 6 to 18;

n is the number of acidic hydrogen atoms in the heteropolyacid and is a number above 1;

y is the number of oxygen atoms in the heteropolyacid and is a number from 10 to 70;

and x is the number of moles of water of crystallization and is a number from 0 to 40.

33. A process according to claim 32, wherein the alcohol is a saturated monoalcohol having 1 to 22 carbon atoms, an ether alcohol of the formula $C_nH_{2n+1}-O-C_nH_{2n+1}-OH$ wherein n is an integer of 1 to 5, a polyol, a mono- or polyethoxylated polyol, or a mono- or polypropoxylated polyol.

34. A process according to claim 33, wherein the alcohol is n-propanol, methanol, ethanol, n-butanol, isopropanol, sec-butanol, tert-butanol, 2-ethylhexanol, methoxyethanol, ethoxyethanol, methoxymethanol, ethoxymethanol, ethylene glycol, propylene glycol, 1,3-butanediol, 1,4-butanediol, 1,6-hexanediol, neopentyl glycol, 1,4-cyclohexanediol, 1,4-cyclohexanedimethanol, 2,2,4-trimethyl-1,3-pentanediol, 2-ethyl-2-methyl-1,3-propanediol, 2,-diethyl-1,3-propanediol, diethylene glycol dipropylene glycol, triethylene glycol, tripropylene glycol, tetraethylene glycol, tetrapropylene glycol, trimethylolethane, trimethylolpropane, glycerol or pentaerythritol.

* * * * *